United States Patent
Carr et al.

(10) Patent No.: US 9,144,493 B2
(45) Date of Patent: Sep. 29, 2015

(54) VALVE PROSTHESIS DEPLOYMENT ASSEMBLY AND METHOD

(71) Applicant: Medtronic Vascular Galway Limited, Ballybrit, Galway (IE)

(72) Inventors: Damian Carr, Ballybrit (IE); Kate Corish, Ballybrit (IE); Niall Duffy, Ballybrit (IE); Ronan Rogers, Ballybrit (IE); Yossi Tuval, Netanaya (IL); Frank White, Ballybrit (IE); Declan Costello, Ballybrit (IE); John Gallagher, Ballybrit (IE); James Kearns, Ballybrit (IE); Edmond Sheahan, Ballybrit (IE); Matthew Rust, Santa Rosa, CA (US)

(73) Assignee: Medtronic Vascular Galway Limited, Ballybrit, Galway (IE)

( * ) Notice: Subject to any disclaimer, the term of this patent is extended or adjusted under 35 U.S.C. 154(b) by 219 days.

(21) Appl. No.: 13/676,414

(22) Filed: Nov. 14, 2012

(65) Prior Publication Data

US 2014/0135909 A1    May 15, 2014

(51) Int. Cl.
*A61F 2/24*   (2006.01)
*A61F 2/966*  (2013.01)
*A61F 2/95*   (2013.01)

(52) U.S. Cl.
CPC .............. *A61F 2/2427* (2013.01); *A61F 2/2436* (2013.01); *A61F 2/966* (2013.01); *A61F 2002/9517* (2013.01)

(58) Field of Classification Search
CPC ... A61F 2/2418; A61F 2/2412; A61F 2/2427; A61F 2002/9517; A61F 2/243
USPC ........... 623/2.11, 1.23, 1.12, 2.17, 1.11, 2.19, 623/2.18
See application file for complete search history.

(56) References Cited

U.S. PATENT DOCUMENTS

| 5,824,041 | A | 10/1998 | Lenker et al. | |
| 6,238,430 | B1 * | 5/2001 | Klumb et al. | 623/1.11 |
| 6,849,084 | B2 * | 2/2005 | Rabkin et al. | 623/1.12 |
| 7,052,511 | B2 * | 5/2006 | Weldon et al. | 623/1.11 |

(Continued)

FOREIGN PATENT DOCUMENTS

| DE | 102006004123 | 8/2007 |
| WO | WO2008/042266 | 4/2008 |

(Continued)

OTHER PUBLICATIONS

PCT/US2013/068555 PCT Search Report and Written Opinion, Mar. 4, 2014.

*Primary Examiner* — Jonathan W Miles
*Assistant Examiner* — George J Ulsh (57) ABSTRACT

The delivery systems disclosed herein can create simultaneous movement of an inner and an outer sheath of the delivery system. The delivery systems can generally include a handle assembly and a delivery catheter. In certain embodiments, the inner shaft and the outer sheath can be slidably controlled by a control element in the handle. The handle assembly can include a housing with a thumbwheel acting as the control element. In certain embodiments, movement of the inner shaft and the outer sheath can be caused via a gear-type system. In certain embodiments, the handle assembly can include a rotatable housing. A control element can rotate the housing, which can cause a first boss associated with the outer sheath and a second boss associated with the inner shaft to move in opposite directions.

24 Claims, 8 Drawing Sheets

(56) References Cited

U.S. PATENT DOCUMENTS

| | | | |
|---|---|---|---|
| 7,722,638 B2 * | 5/2010 | Deyette et al. | 606/200 |
| 7,914,569 B2 | 3/2011 | Nguyen et al. | |
| 8,016,877 B2 | 9/2011 | Sequin et al. | |
| 2004/0127912 A1 | 7/2004 | Rabkin et al. | |
| 2007/0156225 A1 | 7/2007 | George et al. | |
| 2007/0168014 A1 * | 7/2007 | Jimenez et al. | 623/1.12 |
| 2010/0145431 A1 * | 6/2010 | Wu et al. | 623/1.11 |
| 2010/0286768 A1 | 11/2010 | Alkhatib | |
| 2011/0202128 A1 | 8/2011 | Duffy | |
| 2011/0245782 A1 | 10/2011 | Berthiaume et al. | |
| 2012/1581117 | 6/2012 | Ryan | |
| 2012/0172963 A1 | 7/2012 | Ryan et al. | |
| 2012/0221093 A1 | 8/2012 | McHugo | |

FOREIGN PATENT DOCUMENTS

| | | | |
|---|---|---|---|
| WO | WO 2008042266 A2 * | 4/2008 | |
| WO | WO2011/137531 | 11/2011 | |

* cited by examiner

VALVE PROSTHESIS DEPLOYMENT ASSEMBLY AND METHOD

BACKGROUND

1. Field

The present disclosure relates to systems for delivering a prosthesis to a desired location in the body of a patient and methods for delivering and implanting a prosthesis. More particularly, the present disclosure relates to prosthetic valve delivery systems for deploying a heart valve prosthesis within a body lumen and to methods of delivering and deploying such a prosthesis to a desired location in the body.

2. Background

Currently, replacement of a deficient cardiac valve is often performed by placing the patient under extracorporeal circulation, temporarily stopping the heart, opening the thorax (e.g., by a sternotomy), surgically opening the heart, excising the deficient valve, and then implanting a prosthetic valve in its place. This procedure generally requires prolonged patient hospitalization, as well as extensive and often painful recovery.

Recently, minimally invasive approaches have been developed to facilitate catheter-based implantation of valve prostheses in the beating heart, intending to obviate the need for the classic sternotomy and cardiopulmonary bypass. For example, U.S. Pat. No. 8,016,877 to Seguin et al. illustrates a technique and a device for replacing a deficient heart valve by percutaneous route. An expandable prosthetic valve can be compressed about a catheter, inserted inside a body lumen, such as the femoral artery, and delivered to a desired location in the heart. Additionally, U.S. Pat. No. 7,914,569 to Nguyen et al. discloses advancing a catheter containing a prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

Other techniques for delivering prosthetic heart valves via a catheter include transapical and trans-aortic approaches for aortic valve replacement, typically involving the use of an introducer port, i.e., a large-bore overtube, of a trocar. A crimped, framed valve prosthesis reversibly coupled to a delivery catheter can be transcatheterally advanced toward the native valve, where it can either be deployed using a balloon catheter, or, alternatively, using a self-expandable system.

With regard to the structure of the heart valve prosthesis itself, U.S. Pat. No. 7,914,569 to Nguyen et al. describes an example prosthesis for percutaneous transluminal delivery, and is incorporated by reference herein in its entirety. The heart valve prosthesis can have a self-expanding multi-level frame that supports a valve body with a skirt and plurality of leaflets. The frame can be contracted during percutaneous transluminal delivery and expanded to an hourglass shape upon deployment within the native heart valve.

BRIEF SUMMARY

The present disclosure describes delivery systems for implanting a heart valve prosthesis through a trans-aortic pathway. By directly assessing the aorta, it is possible to accurately implant a prosthetic valve without need for cardiopulmonary bypass, although the disclosed delivery systems can also be used with cardiopulmonary bypass. Furthermore, the delivery systems disclosed herein can make it possible to create simultaneous movement of an inner shaft and outer sheath of the delivery device, resulting in quicker deployment and requiring a shorter length of the delivery catheter within the ascending aorta needed to deploy the prosthetic valve. The delivery systems can also facilitate recapture of the valve with fewer complications.

When performing an aortic valve implantation procedure via the trans-aortic access route, deployment of the prosthetic valve can be complicated when the patient has a short ascending aorta. With standard delivery systems, the length within the ascending aorta required to deploy the prosthesis can be greater than the length available provided the patient's anatomical features. In addition, the further a tip of a delivery system travels within a body lumen in order to deploy a prosthesis, the greater the risk the tip will damage other parts of the body lumen. The delivery systems disclosed herein can remedy this problem by creating simultaneous movement of an inner shaft and an outer sheath of the delivery system, which can reduce the length required within the ascending aorta to deploy the prosthesis and minimize the length traveled by the tip of the delivery system when deploying the prosthesis. This can widen the potential patient population for certain procedures, allowing for treatment of patients that would have previously been contraindicated due to a short ascending aorta.

In certain embodiments, the delivery systems disclosed herein can include a handle assembly, which can include a housing and a control element. The delivery systems can also include a delivery catheter extending from the handle assembly. The delivery catheter can include an outer sheath slidably controlled by the control element and an inner shaft slidably controlled by the control element. In certain embodiments, the inner shaft can have a valve retainer and a distal tip. In certain embodiments, the control element can be a thumbwheel having a plurality of protrusions located on the exterior surface of the thumbwheel. In certain embodiments, the delivery systems can include a track having an exterior surface and a plurality of protrusions located on at least a portion of the exterior surface, an outer sheath carrier connected to the track and the outer sheath, an inner shaft carrier having an exterior surface and a plurality of protrusions located on at least a portion of the exterior surface, where the inner shaft carrier is connected to the inner shaft, and a secondary gear having an exterior surface and a plurality of protrusions located on the exterior surface. The protrusions on the thumbwheel can interface with the protrusions on the track, the protrusions on the track can interface with the protrusions on the secondary gear, and the protrusions on the secondary gear can also interface with the protrusions on the inner shaft carrier.

In certain embodiments, the delivery systems can include a handle assembly having a rotatable housing with at least one channel and a control element configured to rotate the housing. In certain embodiments, the handle assembly can also include a boss rail extending axially within the housing, a first boss having a protrusion extending from a surface of the first boss and within the channel, the first boss configured to move axially along the boss rail, and a second boss having a protrusion extending from a surface of the second boss and within the channel, the second boss configured to move axially along the boss rail. The delivery systems can also include a delivery catheter extending from the handle assembly having an outer sheath slidably controlled by the first boss and an inner shaft slidably controlled by the second boss. In certain embodiments, the inner shaft can include a valve retainer. In certain embodiments, the delivery catheter can also include a retaining shaft having a distal tip, such that a prosthesis can be mounted about the retaining shaft and the inner shaft can slide along the retaining shaft. In certain embodiments, rotation of the housing can cause the first boss to move in a first direction and the second boss to move in an opposite direction. In certain embodiments, the outer sheath can move in the direction of the first boss and the inner shaft can move in the direction of the second boss. In certain embodiments, the protrusion of the first boss can extend within a first channel of the housing and the protrusion of the second boss can extend within a second channel of the housing.

Methods of delivering a prosthetic valve using a prosthesis delivery system, such as the delivery systems described herein, are also disclosed. Delivery systems such as those disclosed herein can be inserted into a body lumen and advanced within the body lumen to a deployment location. In certain embodiments, the control element can then be activated to simultaneously retract the outer sheath proximally and advance the inner shaft distally. In certain embodiments activating the control element can include rotating a thumbwheel, where rotating the thumbwheel causes a track and an outer sheath carrier connected to the outer sheath to move in a first direction, movement of the track in the first direction causes a secondary gear to rotate, and the rotation of the secondary gear causes an inner shaft carrier and the inner shaft to move in a second direction. In certain embodiments, rotation of the housing of the handle assembly can cause a first boss to move in a first direction along a boss rail and a second boss to move in a second direction along the boss rail. Generally, retraction of the outer sheath and advancement of the inner shaft can expose the valve prosthesis and cause it to deploy.

BRIEF DESCRIPTION OF THE DRAWINGS

The accompanying figures, which are incorporated herein, form part of the specification and illustrate embodiments of prosthetic valve delivery systems and methods of delivering a valve prosthesis to a desired location in a body of a patient. Together with the description, the figures further serve to explain the principles of and allow for the making and using of the prosthetic valve delivery systems and methods described herein. These figures are intended to be illustrative, not limiting. Although the disclosure is generally described in the context of these embodiments, it should be understood that it is not intended to limit the scope of the disclosure to these particular embodiments. In the drawings, like reference numbers indicate identical or functionally similar elements.

DETAILED DESCRIPTION

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The delivery systems disclosed herein can generally include a handle assembly and a delivery catheter. The delivery catheter can generally include an inner shaft and an outer sheath, both of which can be slidably controlled by a control element in the handle. Multiple embodiments of the delivery system are contemplated. In certain embodiments, the handle assembly can include a housing with a thumbwheel acting as the control element. In certain embodiments, movement of the inner shaft and the outer sheath can be caused via a gear-type system. Rotation of the thumbwheel can drive movement of a track located within the handle. The track can have an outer sheath carrier connected to the outer sheath. Movement of the track can cause movement of a secondary gear that interfaces with the track and an inner shaft carrier which is connected to the inner shaft. Thus, rotation of the thumbwheel can cause movement of both the inner shaft and the outer sheath. In certain embodiments, the handle assembly can include a rotatable housing having at least one channel. A control element can rotate the housing, which can cause a first boss associated with the outer sheath and a second boss associated with the inner shaft to move in opposite directions. Thus, rotation of the housing by the control element can cause movement of both the inner shaft and the outer sheath.

FIGS. 1A-2D illustrate delivery system 100, according to an embodiment. Delivery system 100 can include handle 102 and delivery catheter 202. In certain embodiments, handle 102 can include housing 108, thumbwheel 104, track 110, inner shaft carrier 112, outer sheath carrier 118 and secondary gear 114. In certain embodiments, delivery catheter 202 can include outer sheath 124, capsule 126, inner shaft 116, retaining shaft 130, valve retainer 132, and distal tip 128.

Figure 1A:
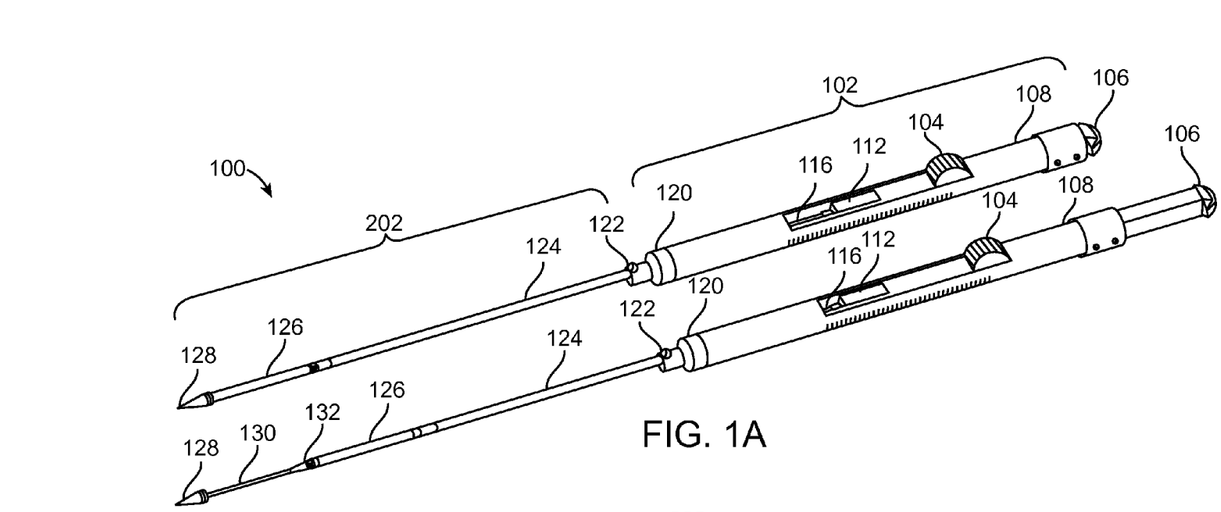
FIG. 1A illustrates the delivery system, according to an embodiment.

In certain embodiments, a distal end of housing 108 can include housing tip 120, through which outer sheath 124 and inner shaft 116 can pass. In certain embodiments, housing tip 120 can be tapered to provide a smooth transition between housing 108 and outer sheath 124. In certain embodiments, housing tip 120 can include flush port 122, which can be used, for example, to introduce fluid into delivery system 100.

Figure 1B:
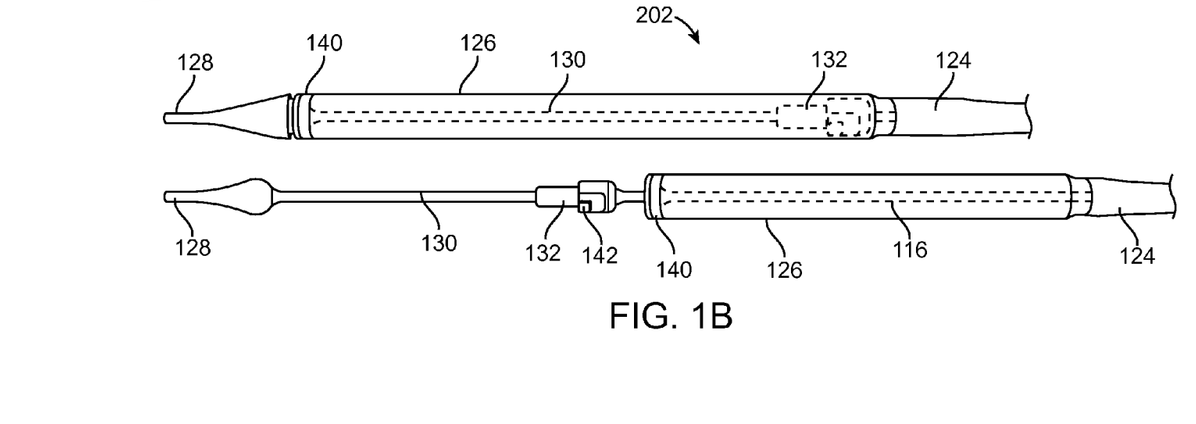
FIG. 1B shows a close-up view of the delivery catheter, according to an embodiment.
Figure 2A:
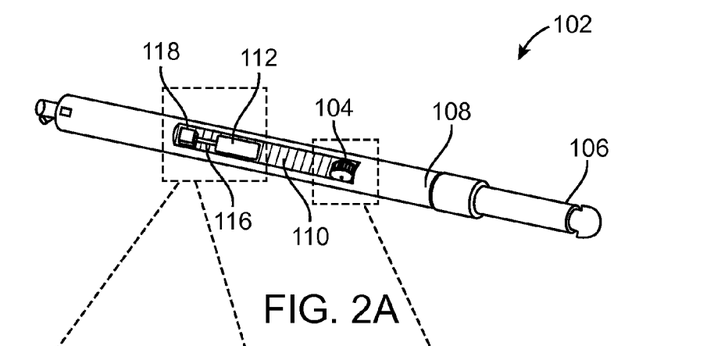
FIGS. 2A-2D illustrate close-up views of the handle assembly, according to an embodiment.
Figure 2B:
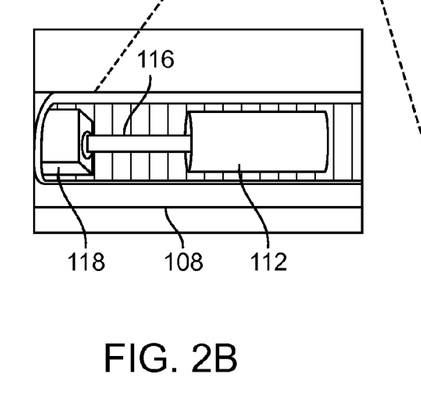
Figure 2C:
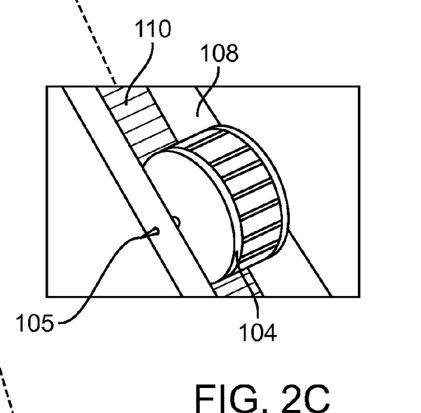
Figure 2D:
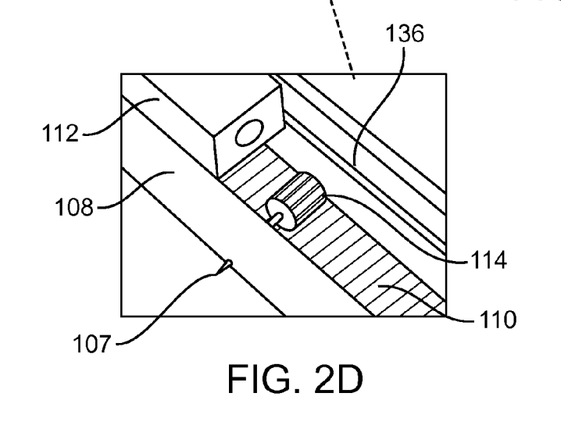

FIG. 1B illustrates a close-up view of delivery catheter 202 in both a delivery configuration and a deployment configuration, according to an embodiment. In certain embodiments, delivery catheter 202 can be a cylindrical polymer sleeve, configured to retain a heart valve prosthesis, although any suitable material can be used. In certain embodiments, outer sheath 124 can include capsule 126 to house the valve prosthesis. In certain embodiments, capsule 126 can have a larger diameter than outer sheath 124. In certain embodiments, capsule 126 can include capsule ring 140. In certain embodiments, capsule ring 140 can be a radiopaque material, which can facilitate positioning of delivery system 100 within a body lumen using medical imaging. In certain embodiments, inner shaft 116 can include distal tip 128, which can be an atraumatic tip to prevent damage to the body lumen as delivery system 100 is advanced through the body. In certain embodiments, distal tip 128 can be tapered from a proximal to a distal end and can include an opening at its distal end to allow delivery system 100 to pass over a guide wire. In certain embodiments, distal tip 128 can be radiopaque to facilitate locating delivery system 100 within the body using medical imaging.

In certain embodiments, inner shaft 116 can include retaining shaft 130. In certain embodiments, retaining shaft 130 can be connected to inner shaft 116 by valve retainer 132. In certain embodiments, retaining shaft 130 can have a smaller diameter than inner shaft 116, and inner shaft 116 can slide along retaining shaft 130. Valve retainer 132 can facilitate retaining a prosthetic valve during delivery while the valve is mounted about retaining shaft 130. In certain embodiments, valve retainer 132 can include retaining elements 142, which can be, for example, a protrusion or indentation on the surface of valve retainer 132. In certain embodiments, retaining elements 142 can correspond to an element on the prosthetic valve to releasably mate the prosthetic valve and retaining elements 142 during delivery.

FIGS. 2A-2D illustrate close-up views of handle 102 and components of handle 102. Housing 108, as well as the other components of handle 102, can be made from any suitable material, for example, plastic or metal. Generally, housing 108 can be a cylindrical tube configured to house the various components, although housing 108 can be any shape. In certain embodiments, handle 102 can include thumbwheel 104, which can act as the control element for delivery system 100. It is understood that alternative control elements can be used instead of thumbwheel 104, for example, knobs, slides, or buttons. In certain embodiments, thumbwheel 104 can be located within housing 108 and mounted on pin 105, about which thumbwheel 104 can rotate. In certain embodiments, at least a portion of thumbwheel 104 can be exposed outside of housing 108 for access by a user. Thumbwheel 104 can interface with track 110, for example, by teeth located on the surfaces of thumbwheel 104 and track 110. It is understood that in addition to teeth, any such interface mechanism can be used, for example, gear-type protrusions or frictional interfacing.

By rotating thumbwheel 104, track 110 can be moved in a first direction, for example, proximally. When track 110 is moved in the proximal direction, proximal track end 106 can exit an opening at the proximal end of housing 108. Track 110 can be connected to outer sheath carrier 118, which can be connected to outer sheath 124. Thus, as track 110 moves in the proximal direction, outer sheath 124 moves in the proximal direction as well. Similarly, thumbwheel 104 can be rotated in an opposite direction, which can move track 110 and outer sheath 124 distally, for example, to recapture a prosthesis. Track 110 can interface with secondary gear 114, for example, by teeth located on the surfaces of track 110 and secondary gear 114. In certain embodiments, secondary gear 114 can be mounted on pin 107. Movement of track 110 can cause rotation of secondary gear 114. Secondary gear 114 can interface with inner shaft carrier 112, for example, by teeth located on the exterior surfaces of secondary gear 114 and inner shaft carrier 112. Rotation of secondary gear 114 can cause movement of inner shaft carrier 112, which is attached to inner shaft 116, in a direction opposite of track 110.

Figure 3:
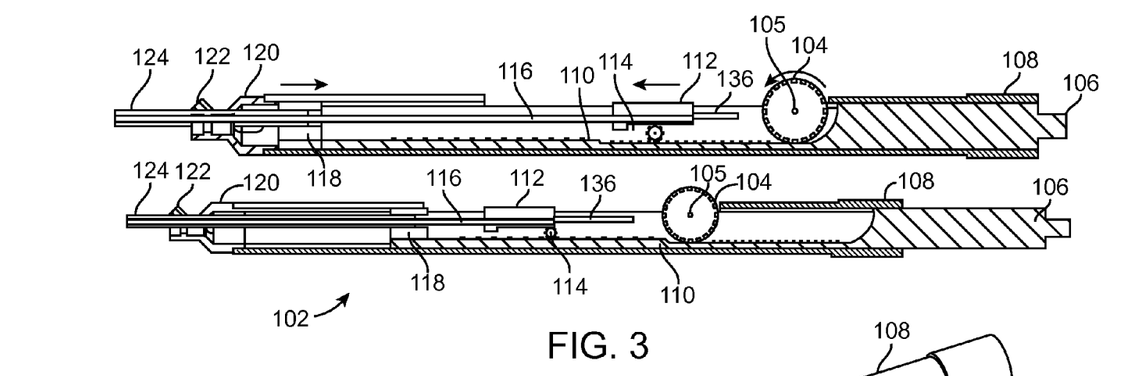
FIG. 3 illustrates an interior view of the handle assembly, according to an embodiment.

FIG. 3 illustrates an interior view of handle 102, according to an embodiment. As shown in FIG. 3, rotation of thumbwheel 104 toward the distal direction can cause movement of track 110 in the proximal direction. Proximal track end 106 can move proximally out of an opening at the proximal end of housing 108. Outer sheath carrier 118 can be connected to track 110, and can also move in the proximal direction as track 110 moves in the proximal direction. In certain embodiments, outer sheath carrier 118 can also be connected to outer sheath 124. Thus, outer sheath 124 can be retracted in the proximal direction along with track 110. Movement of track 110 in the proximal direction can cause rotation of secondary gear 114 in the distal direction. In certain embodiments, secondary gear 114 can interface with inner shaft carrier 112. Thus, rotation of secondary gear 114 in the distal direction can cause movement of inner shaft carrier 112 in the distal direction. Inner shaft carrier 112 can be connected to inner shaft 116. Thus, as shown, for example, in FIG. 1A, as inner shaft carrier 112 moves in the distal direction, inner shaft 116 can also move in the distal direction. In certain embodiments, inner shaft 116 can pass through outer sheath carrier 118 and within outer sheath 124, which can allow simultaneous movement of inner shaft 116 and outer sheath 124.

Figure 4:
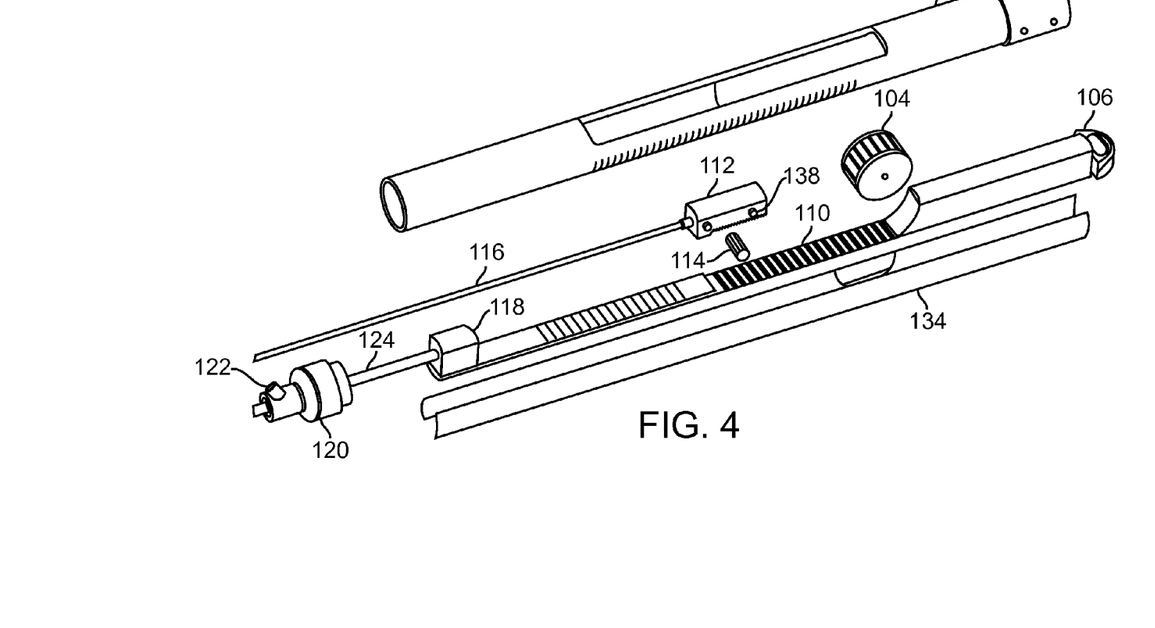
FIG. 4 illustrates a dismantled representation of the handle assembly, according to an embodiment.

FIG. 4 illustrates a dismantled view of handle 102, according to an embodiment. In certain embodiments, handle 102 can include guide rails 134. Guide rails 134 can facilitate smooth axial movement of track 110 within housing 108. In certain embodiments, guide rails 134 can include slots 136, shown in FIG. 3, which can accommodate protrusions 138 of inner shaft carrier 112. This can facilitate smooth axial movement of inner shaft carrier 112 within housing 108.

FIGS. 5A-5D illustrate an embodiment of delivery system 500. Delivery system 500 can include handle 502, sheath 524, and inner shaft 516. In certain embodiments, inner shaft 516 can include valve retainer 532. In certain embodiments, delivery system 500 can also include retaining shaft 530 having delivery tip 528. In certain embodiments, inner shaft 516 can slide axially along retaining shaft 530.

In certain embodiments, handle 502 can include housing 508, thumbwheel 504, and boss housing 522. In certain embodiments, boss housing 522 can have a covering (not shown) that is linked to boss housing 522. The covering can be made of any material, for example, plastic or rubber, and can facilitate gripping handle 502. In certain embodiments, boss housing 522 can contain boss rail 506, which can have sheath boss 512 and retainer boss 514 slidably disposed along boss rail 506. In certain embodiments, boss housing 522 can include sheath boss channel 513 and retainer boss channel 515. Sheath boss 512 and retainer boss 514 can each include boss guide 518, shown in FIGS. 6A-7B, protruding from a surface of the respective boss, which can fit within sheath boss channel 513 and retainer boss channel 515, respectively.

Figure 6A:
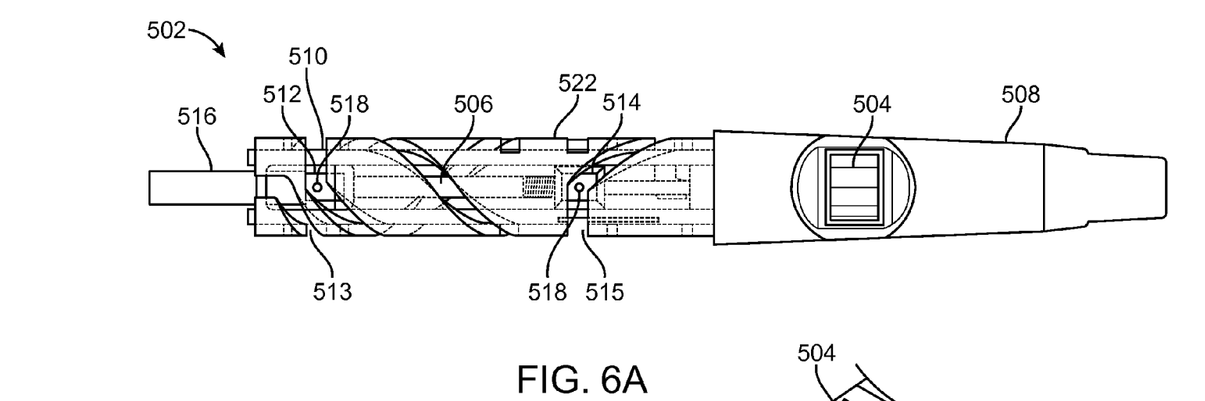
FIGS. 6A-6B illustrate a close-up view of the handle assembly, according to an embodiment.
Figure 6B:
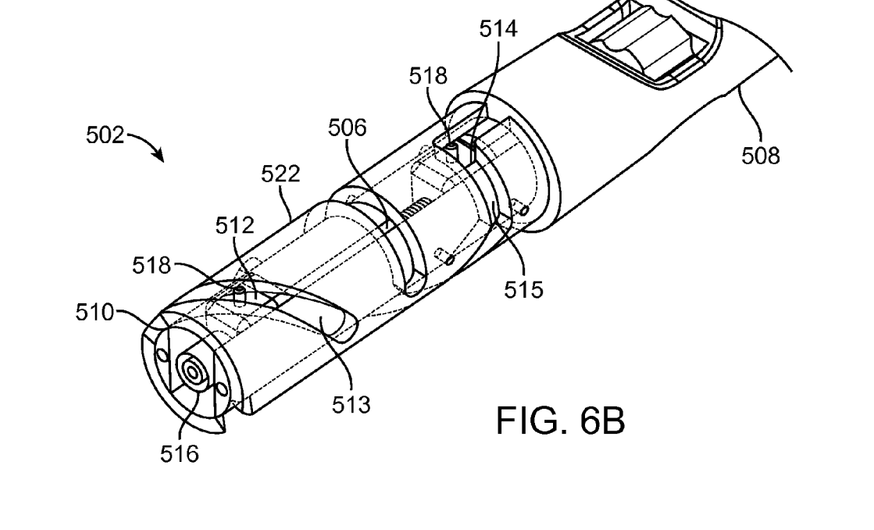

FIGS. 6A-6B illustrate close-up views of handle 502. Boss housing 522 can be made of any suitable material, for example, plastic or metal. In certain embodiments, handle 502 can include boss rail 506 within boss housing 522. Sheath boss 512 and retainer boss 514 can be configured to slide axially along boss rail 506. In certain embodiments, side rails 510 can be included within boss housing 522 to facilitate smooth axial movement of retainer boss 514 and sheath boss 512.

In certain embodiments, boss housing 522 can include sheath boss channel 513 and retainer boss channel 515. In certain embodiments, these channels can be a single channel along boss housing 522. Sheath boss 512 and retainer boss 514 can each have boss guide 518, which can fit within its respective channel. In certain embodiments, sheath boss channel 513 and retainer boss channel 515 can be non-uniform such that rotation of boss housing 522 causes sheath boss 512 and retainer boss 514 to move axially at different rates. For example, when a channel is perpendicular to the axis of boss rail 506, no force is applied to boss guide 518 by boss housing 522. Therefore, the boss and its associated shaft will not move. However, when the channel is at an angle and rotating about the axis of boss rail 506, boss housing 522 applies force to boss guide 518, causing the boss to move along boss rail 506. Depending on the design of channels 513 and 515, bosses 512 and 514, and thus sheath 524 (not shown) and inner shaft 516, can move at the same time, individually, and at varying rates and distances. For example, if boss housing 522 is rotated and retainer boss channel 515 is perpendicular to the axis of boss rail 506 while sheath boss channel 513 is at an angle, retainer boss 514 and associated inner shaft 516 will not move, while sheath boss 512 and sheath 524 will move.

Other mechanisms are contemplated for controlling the rate at which inner shaft 516 and sheath 526 move to compensate for the foreshortening of the prosthetic valve during implantation. For example, a gearing system can be used. The gear ratios can be designed such that inner shaft 516 moves at a rate that compensates for or is equal to the foreshortening of the prosthetic valve during implantation. This can facilitate accurate placement of the prosthetic valve. For example, a valve 60 mm in length in its delivery configuration that shortens by 10 mm to 50 mm in length in its deployed configuration can make accurate placement of the prosthetic valve in a patient difficult. To compensate for the foreshortening of the valve, the inner shaft of the delivery system can be designed to move 10 mm in one direction while the outer sheath of the delivery system can be designed to move 60 mm in the opposite direction thereby compensating for the foreshortening of the valve and thus facilitating its accurate placement.

Figure 5A:
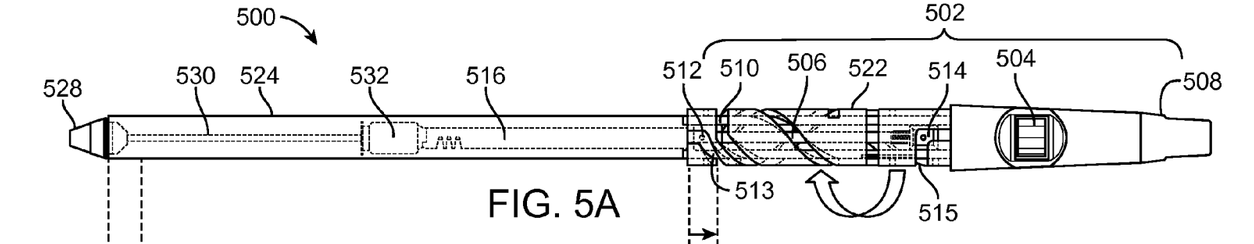
FIGS. 5A-5D illustrate the delivery system, according to an embodiment.
Figure 5B:
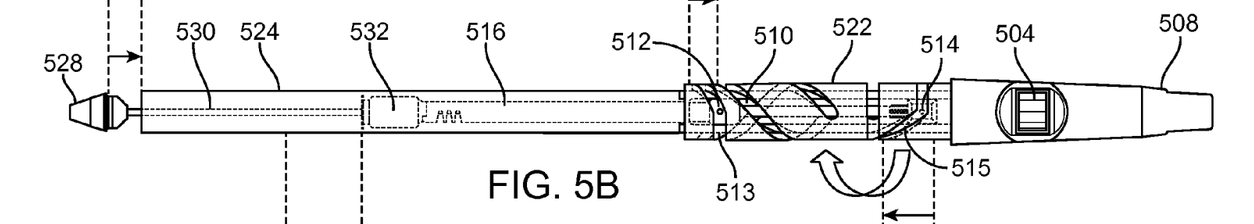
Figure 5C:
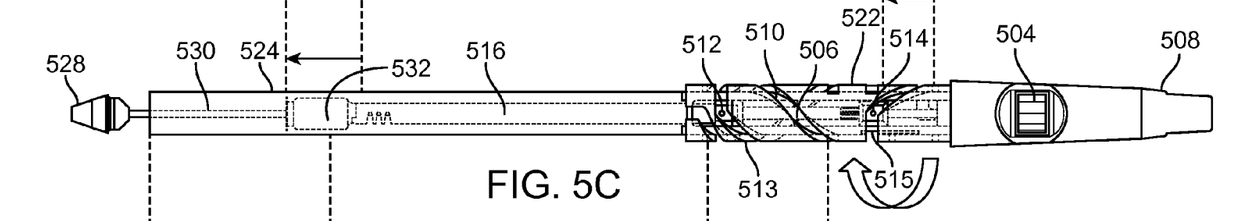
Figure 5D:
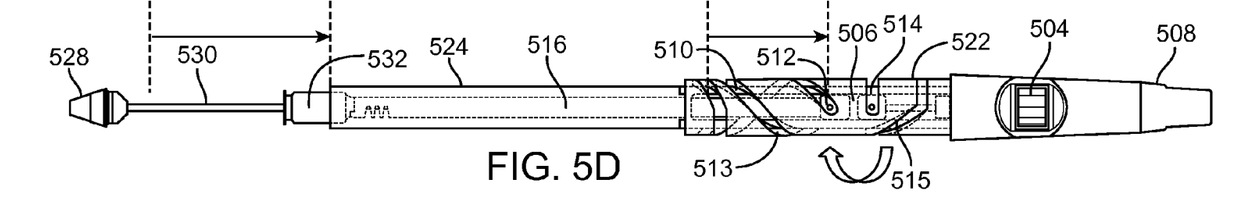

FIGS. 5A-5D illustrate a delivery sequence for delivery system 500, according to an embodiment. FIG. 5A illustrates delivery system 500 in a delivery configuration. In certain embodiments, a covering (not shown) linked to boss housing 522 can be rotated, which can rotate boss housing 522. In certain embodiments, thumbwheel 504 can be rotated, which can rotate boss housing 522. Rotating boss housing 522 can force boss guide 518 of sheath boss 512 through sheath boss channel 513. Sheath boss 512 thus moves in the proximal direction along boss rail 506, therefore moving sheath 524 in the proximal direction, as indicated by the arrows in FIG. 5B. As shown in FIG. 5C, as boss housing 522 continues to rotate, retainer boss 514 can move in the distal direction along boss rail 506. Thus, inner shaft 516 can also move in the distal direction, as indicated by the arrow in FIG. 5C. In certain embodiments, inner shaft 516 can move along retaining shaft 530, which can push the prosthesis in the distal direction. This can facilitate deployment of the support arms of the prosthesis, and can also offset the decrease in the length of the prosthesis as it moves from a delivery configuration to a deployment configuration. As boss housing 522 rotates even further, as shown in FIG. 5D, sheath boss 512 can continue to move in the proximal direction, therefore retracting sheath 524 further in the proximal direction, fully exposing the prosthesis and allowing it to deploy.

Figure 7A:
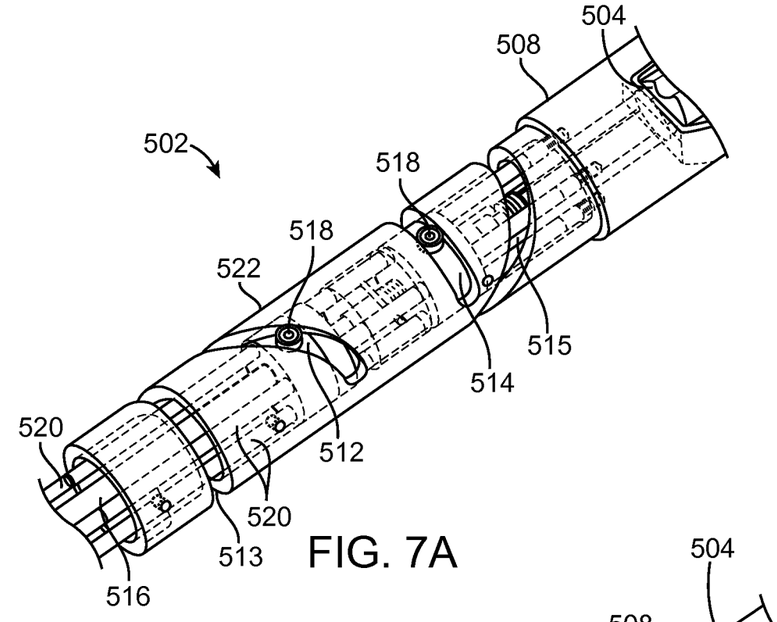
FIGS. 7A-7B illustrate an interior view of the handle assembly, according to an embodiment.
Figure 7B:
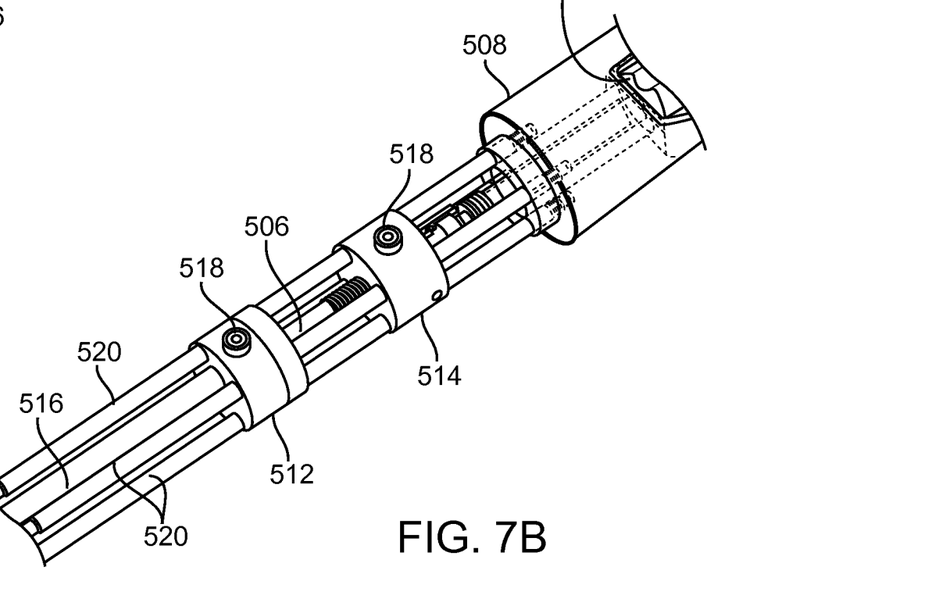

FIGS. 7A-7B illustrate an interior view of an embodiment of handle 502. In addition to boss rail 506, handle 502 can include guide bars 520. Guide bars 520 can extend through sheath boss 512 and retainer boss 514 to smoothly guide the bosses in the axial direction. Any number of guide bars 520 can be used. In certain embodiments, guide bars 520 can be spaced circumferentially about a central axis of bosses 512 and 514, in either a uniform or non-uniform pattern. In certain embodiments, boss rail 506 can be excluded such that sheath boss 512 and retainer boss 514 are supported only along guide bars 520.

Figure 8A:
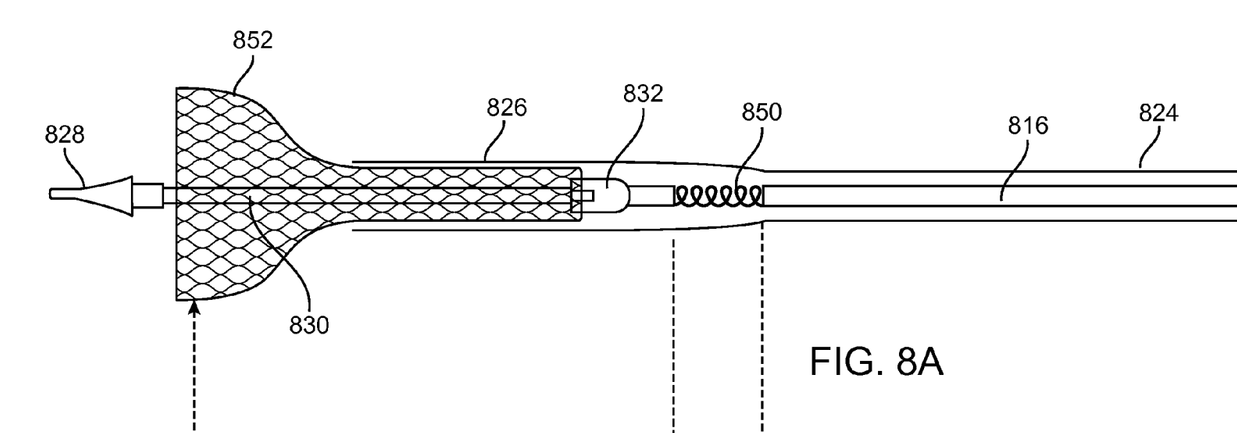
FIGS. 8A-8B illustrate a spring joint mechanism between the inner shaft and valve retainer, according to an embodiment.
Figure 8B:
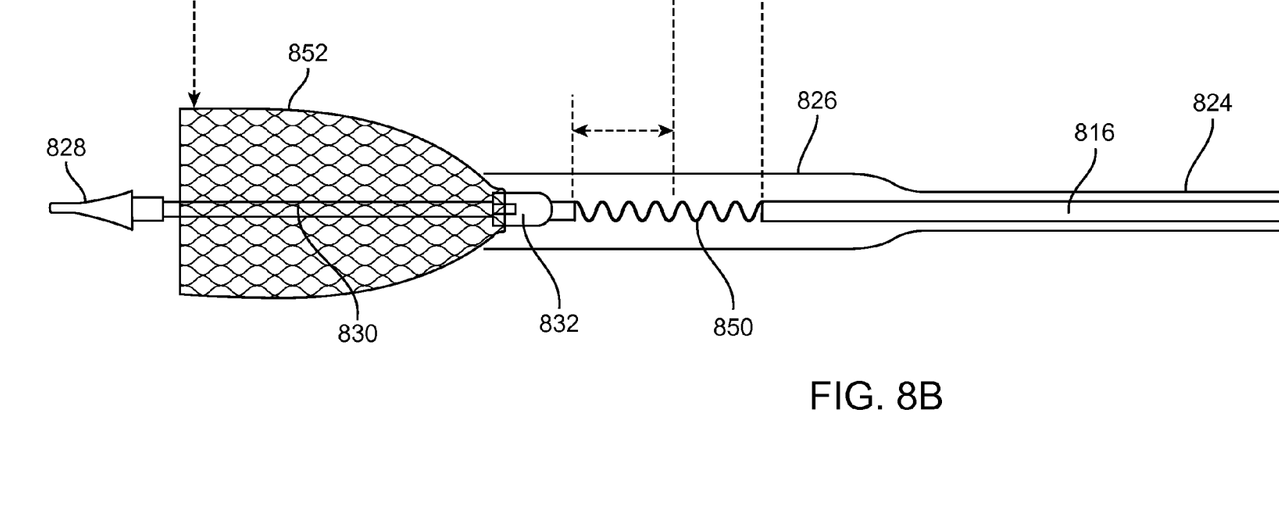

FIGS. 8A-8B illustrate an embodiment of the delivery system including spring joint 850. Spring joint 850 can facilitate stabilizing the position of prosthesis 852 during deployment. In certain embodiments, spring joint 850 can be located between valve retainer 832 and inner shaft 816. Spring joint 850 can be made of any suitable material, for example, metal. In certain embodiments, spring joint 850 can be made of a shape-memory alloy, such that when spring joint 850 is released from a compressed configuration, spring joint 850 expands to a predetermined length. The material properties of spring joint 850 can determine the rate at which spring joint 850 expands.

Spring joint 850 can be designed to be activated only upon deployment of prosthesis 852. For example, as outer sheath 824 and capsule 826 are retracted in the proximal direction, capsule 826 can release a mechanism that allows spring joint 850 to expand in the distal direction. In certain embodiments, spring joint 850 can be activated by a button on the handle or the release of a tether attached to spring joint 850. Activation of spring joint 850 can force valve retainer 832 distally to maintain the position of the distal end of prosthesis 852 as it is deployed from its delivery configuration, which is longer than its deployment configuration. This can compensate for the change in length of prosthesis 852 from its delivery configuration to its deployment configuration and keep the distal end of prosthesis 852 in a fixed position to prevent movement of prosthesis 852 from the desired deployment location within the body.

Figure 9A:
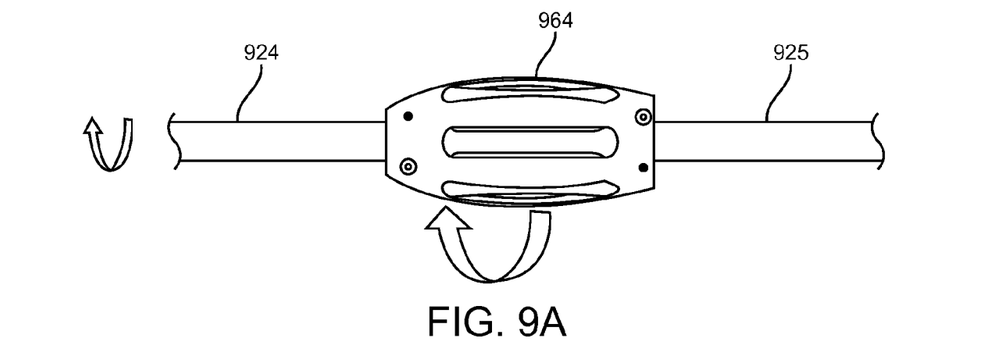
FIGS. 9A-9D illustrate a rotatable hub, interior views of the hub and a valve retainer, according to an embodiment.
Figure 9B:
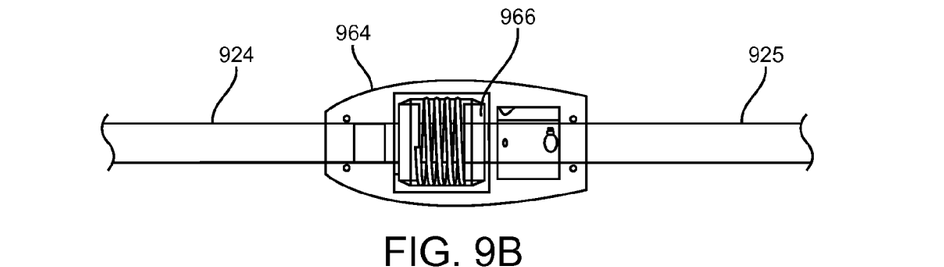
Figure 9C:
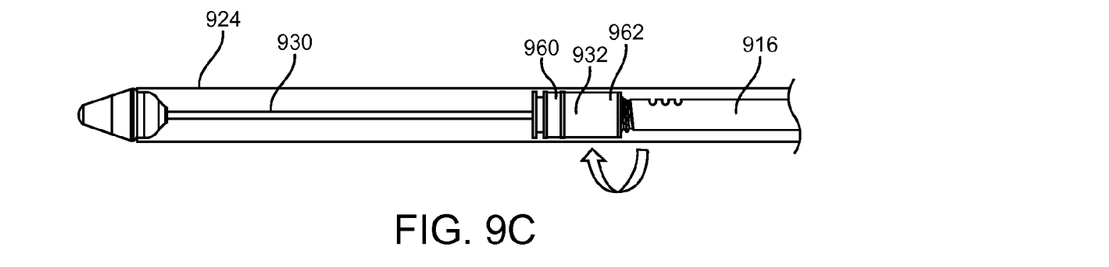
Figure 9D:
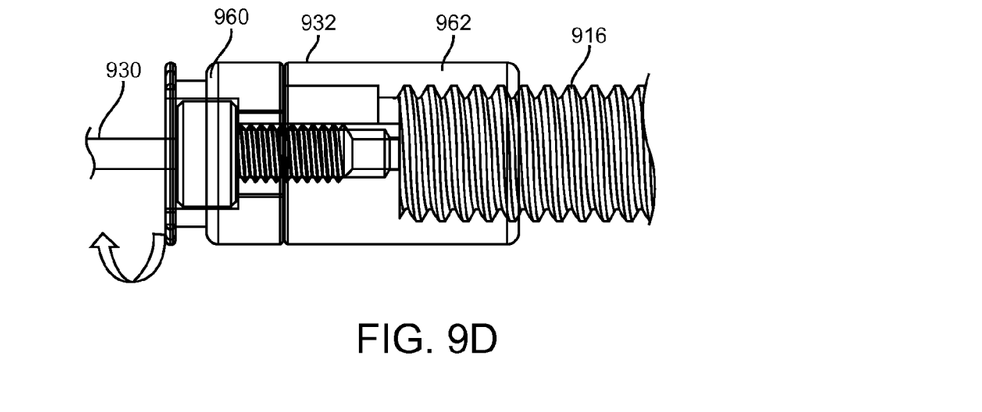

FIGS. 9A-9D illustrate rotatable hub 964, according to an embodiment. In certain embodiments, rotatable hub 964 can be located along and rotate about the outer sheath. Rotatable hub 964 can allow rotation of distal outer sheath portion 924 while proximal outer sheath portion 925 remains fixed. As shown in FIG. 9B, an interior of rotatable hub 964 can include a sealing mechanism 966, which can allow distal outer sheath portion 924 to be decoupled from proximal outer sheath portion 925 within rotatable hub 964. FIG. 9C illustrates that rotatable hub 964 can be rotated, such that distal outer sheath portion 924 also rotates. Further, FIG. 9D illustrates that, as rotatable hub 964 and distal outer sheath portion 924 rotate, so can distal valve retainer portion 960 of distal valve retainer 932. Proximal valve retainer portion 962 and inner shaft 916, however, can remain fixed. Enabling rotation of distal outer sheath portion 924 and distal valve retainer portion 960 can allow the prosthetic valve loaded about retaining shaft 930 to be oriented within the native valve.

Methods of delivering a heart valve prosthesis are also disclosed. References to the figures are made by way of example, and are not meant to be limiting. Prior to the procedure, the desired valve implantation location can be determined. This can be done with assistance of medical imaging, such as a CT scan. For trans-aortic prosthetic valve implantation, the implantation location can generally be located within an aortic sinus such that the distal part of the heart valve prosthesis engages the leaflets of the native aortic valve, and the proximal part of the heart valve prosthesis engages the inner wall of the ascending aorta. Alternative implantation sites can be used, and the optimal implantation site can be determined for each individual patient.

Generally, for a trans-aortic procedure, the chest can be prepared and the ascending aorta can be accessed, such as by a mini-sternotomy or a thoracotomy. In certain embodiments, the user can place delivery system 100 over a guide wire and advance delivery system 100 through the ascending aorta. In certain embodiments, medical imaging can be used to locate features of delivery system 100 to facilitate positioning delivery system 100 at the desired deployment location.

Once in the desired anatomical position, a user can activate a control element, for example, by rotating thumbwheel 104 in a distal direction. Rotation of thumbwheel 104 toward the distal direction can cause movement of track 110, and thus outer sheath carrier 118 and outer sheath 124, in the proximal direction. Movement of track 110 in the proximal direction can cause rotation of secondary gear 114 in the distal direction, which can cause movement of inner shaft carrier 112, and thus inner shaft 116, in the distal direction. This can expose and deploy support arms of the valve prosthesis. Still further rotation of thumbwheel 104 can further retract outer sheath 124 in the proximal direction to expose and deploy the entire valve prosthesis.

In certain embodiments, rotation of thumbwheel 504 can rotate boss housing 522. In certain embodiments, boss housing 522 can have a covering (not shown) that is linked to boss housing 522. The covering can be directly manipulated to rotate boss housing 522. Rotation of boss housing 522 can force boss guide 518 of sheath boss 512 through sheath boss channel 513, which can move sheath boss 512 along boss rail 506, for example in the proximal direction, therefore moving sheath 524 in the proximal direction. As boss housing 522 continues to rotate, retainer boss 514 can move in the distal direction along boss rail 506, which can move inner shaft 516 in the distal direction. In certain embodiments, inner shaft 516 can move along retaining shaft 530, which can push the prosthesis in the distal direction. This can facilitate deployment of the support arms of the prosthesis, and can also offset the decrease in the length of the prosthesis as it moves from a delivery configuration to a deployment configuration. As boss housing 522 rotates even further, sheath boss 512 can continue to move in the proximal direction, therefore retracting sheath 524 further in the proximal direction, fully exposing the prosthesis and allowing it to deploy.

In certain embodiments, as outer sheath 824 and capsule 826 are retracted in the proximal direction, capsule 826 can release a mechanism that allows spring joint 850 to expand in the distal direction. In certain embodiments, a button on the handle can be pressed or a tether released in order to activate spring joint 850. Activation of spring joint 850 can force valve retainer 832 distally to maintain the position of the distal end of prosthesis 852 as it is deployed from its delivery configuration. In certain embodiments, rotatable hub 964 can be rotated prior to full deployment of the prosthesis, such that distal outer sheath portion 924 and distal valve retainer portion 960 also rotate. This can allow the prosthetic valve loaded about retaining shaft 930 to be oriented within the native valve.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A prosthesis delivery system comprising: a handle assembly comprising: a housing; and a control element comprising a thumbwheel with an exterior surface having a plurality of protrusions located on the exterior surface; and a delivery catheter extending from the handle assembly comprising: an outer sheath slidably controlled by the control element; and an inner shaft slidably controlled by the control element, the inner shaft having a valve retainer; a track having an exterior surface and a plurality of protrusions located on at least a portion of the exterior surface; an outer sheath carrier connected to the track and the outer sheath; an inner shaft carrier, having an exterior surface and a plurality of protrusions located on at least a portion of the exterior surface, connected to the inner shaft; and a secondary gear having an exterior surface and a plurality of protrusions located on the exterior surface, wherein the protrusions on the thumbwheel directly interface with the protrusions on the track, the protrusions on the track directly interface with the protrusions on the secondary gear, and the protrusions on the secondary gear also directly interface with the protrusions on the inner shaft carrier.

2. The delivery system of claim 1, wherein the inner shaft extends through the outer sheath carrier.

3. The delivery system of claim 1, wherein rotation of the thumbwheel causes the track to move in a first direction and the inner shaft carrier to move in an opposite direction.

4. The delivery system of claim 3, wherein the track moves in a proximal direction out of an opening at a proximal end of the housing.

5. The delivery system of claim 1, wherein the outer sheath further comprises a valve capsule at a distal end of the outer sheath configured to house a prosthetic valve.

6. The delivery system of claim 5, wherein the prosthetic valve is a prosthetic heart valve.

7. The delivery system of claim 1, further comprising at least one guide rail within the housing configured to axially guide the track and the inner shaft carrier.

8. The delivery system of claim 7, wherein the guide rail comprises at least one slot configured to interface with at least one protrusion on the inner shaft carrier to permit axial movement of the inner shaft carrier along the guide rail.

9. The delivery system of claim 1, wherein the delivery catheter further comprises a retaining shaft having a distal tip, wherein the inner shaft is configured to move axially along the retaining shaft.

10. The delivery system of claim 9, further comprising:
at least one channel along the housing;
a boss rail extending axially within the housing;

a first boss having a protrusion extending from a surface of the first boss and within the channel, the first boss configured to move axially along the boss rail; and a second boss having a protrusion extending from a surface of the second boss and within the channel, the second boss configured to move axially along the boss rail;

wherein the housing comprises a rotatable housing, the control element is configured to rotate the housing, the outer sheath is slidably controlled by the first boss, and the inner shaft is slidably controlled by the second boss.

11. The delivery system of claim 10, wherein rotation of the housing causes the first boss to move in a first direction and the second boss to move in an opposite direction.

12. The delivery system of claim 11, wherein the outer sheath moves in the direction of the first boss and the inner shaft moves in the direction of the second boss.

13. The delivery system of claim 11, wherein the first boss moves further than the second boss.

14. The delivery system of claim 10, wherein the channel extends circumferentially around the housing in a non-uniform pattern.

15. The delivery system of claim 10, wherein the protrusion of the first boss extends within a first channel and the protrusion of the second boss extends within a second channel.

16. The delivery system of claim 10, further comprising at least one guide bar parallel to the boss rail, extending through the first boss and the second boss, along which the first boss and the second boss move axially.

17. The delivery system of claim 10, wherein the outer sheath further comprises a valve capsule at a distal end of the outer sheath configured to house a prosthetic valve.

18. The delivery system of claim 17, wherein the prosthetic valve is a prosthetic heart valve.

19. The delivery system of claim 1, further comprising an expansion joint located along the inner shaft proximally from the valve retainer, wherein the expansion joint is configured to expand in a distal direction as the outer sheath is retracted in a proximal direction.

20. The delivery system of claim 1, further comprising a rotatable hub configured to rotate a distal portion of the outer sheath and a distal portion of the valve retainer.

21. A method of delivering a prosthetic heart valve with a prosthesis delivery system, the prosthesis delivery system comprising: a handle assembly comprising: a housing; and a control element; and a delivery catheter extending from the handle assembly comprising: an outer sheath slidably controlled by the control element; and an inner shaft slidably controlled by the control element, the inner shaft having a valve retainer; the method comprising: inserting the delivery catheter into a body lumen; advancing the delivery catheter within the body lumen to a deployment location; activating the control element to simultaneously retract the outer sheath proximally and advance the inner shaft distally, and wherein the handle assembly further comprises: a thumbwheel having an exterior surface and a plurality of protrusions located on the exterior surface; a track having an exterior surface and a plurality of protrusions located on at least a portion of the exterior surface; an outer sheath carrier connected to the track and the outer sheath; an inner shaft carrier, having an exterior surface and a plurality of protrusions located on at least a portion of the exterior surface, connected to the inner shaft; and a secondary gear having an exterior surface and a plurality of protrusions located on the exterior surface; wherein the protrusions on the thumbwheel directly interface with the protrusions on the track, the protrusions on the track directly interface with the protrusions on the secondary gear, and the protrusions on the secondary gear also directly interface with the protrusions on the inner shaft carrier, and wherein activating the control element comprises rotating the thumbwheel, wherein rotating the thumbwheel causes the track and the outer sheath to move in a first direction, wherein movement of the track in the first direction causes the secondary gear to rotate, and wherein rotation of the secondary gear causes the inner shaft carrier and the inner shaft to move in a second direction.

22. The method of claim 21, wherein the handle assembly further comprises:
  at least one channel along the housing;
  a boss rail extending axially within the housing;
  a first boss having a protrusion extending from a surface of the first boss and within the channel, the first boss configured to move axially along the boss rail; and
  a second boss having a protrusion extending from a surface of the second boss and within the channel, the second boss configured to move axially along the boss rail;
  wherein the housing comprises a rotatable housing, the control element is configured to rotate the housing, the outer sheath is slidably controlled by the first boss, and the inner shaft is slidably controlled by the second boss,
  wherein rotating the housing causes the first boss to move in a first direction along the boss rail and the second boss to move in a second direction along the boss rail.

23. The method of claim 22, wherein movement of the first boss in the first direction causes the outer sheath to move in the first direction, and wherein movement of the second boss in the direction causes the inner shaft to move in the second direction.

24. The method of claim 21, further comprising rotating a hub about the outer sheath configured to rotate a distal portion of the outer sheath and a distal portion of the valve retainer to orient a prosthetic valve mounted on the inner shaft.

* * * * *